United States Patent
Clark et al.

(10) Patent No.: US 6,611,717 B1
(45) Date of Patent: Aug. 26, 2003

(54) IMPLANT DEVICE

(75) Inventors: Graeme Milbourne Clark, Eltham; Lawrence Thomas Cohen, North Blackburn; Peter Andrew Busby, Caulfield, all of (AU)

(73) Assignee: The University of Melbourne, Victoria (AU)

( * ) Notice: Subject to any disclaimer, the term of this patent is extended or adjusted under 35 U.S.C. 154(b) by 0 days.

(21) Appl. No.: 08/762,604

(22) Filed: Dec. 9, 1996

Related U.S. Application Data

(63) Continuation of application No. 08/397,155, filed as application No. PCT/AU94/00370 on Jul. 1, 1994, now abandoned.

(30) Foreign Application Priority Data

Jul. 1, 1993 (AU) .............................................. PL9748

(51) Int. Cl.⁷ ................................................. A61N 1/36
(52) U.S. Cl. ......................................................... 607/56
(58) Field of Search ............................. 607/55, 56, 57, 607/59, 60, 62, 136, 137; 623/10, 24, 25, 12

(56) References Cited

U.S. PATENT DOCUMENTS

| | | | | |
|---|---|---|---|---|
| 4,400,590 A | * | 8/1983 | Michelson | 179/107 FD |
| 4,441,202 A | | 4/1984 | Tong et al. | 381/68 |
| 4,515,158 A | | 5/1985 | Patrick et al. | 128/419 |
| 4,532,930 A | * | 8/1985 | Crosby et al. | 128/419 R |
| 4,592,359 A | * | 6/1986 | Galbraith | 128/419 R |
| 4,593,696 A | * | 6/1986 | Hochmair et al. | 381/68 |
| 4,648,403 A | | 3/1987 | Van Compernolle | 128/419 |
| 4,813,417 A | | 3/1989 | Soli et al. | 128/420.5 |
| 4,823,795 A | | 4/1989 | van den Honert | 128/420.5 |
| 4,947,844 A | * | 8/1990 | McDermott | 128/421 |
| 5,061,282 A | | 10/1991 | Jacobs | 623/10 |
| 5,095,904 A | | 3/1992 | Seligman et al. | 128/420.6 |
| 5,095,907 A | * | 3/1992 | Seligman et al. | 623/10 |
| 5,215,085 A | | 6/1993 | von Wallenberg-Pachaly | 128/420.6 |
| 5,522,865 A | * | 6/1996 | Schulman et al. | 607/56 |
| 5,531,774 A | * | 7/1996 | Schulman et al. | 607/56 |
| 5,549,658 A | * | 8/1996 | Shannon et al. | 607/57 |
| 5,569,307 A | * | 10/1996 | Schulman et al. | 607/56 |
| 5,603,726 A | * | 2/1997 | Schulman et al. | 607/57 |
| 5,609,616 A | * | 3/1997 | Schulman et al. | 607/56 |

FOREIGN PATENT DOCUMENTS

| | | |
|---|---|---|
| AU | 1819483 | 2/1984 |
| WO | WO9208330 | 5/1992 |

* cited by examiner

*Primary Examiner*—David J. Isabella
(74) *Attorney, Agent, or Firm*—Gottleib, Rackman & Reisman, P.C.

(57) ABSTRACT

An improved cochlear implant and method of stimulating are disclosed. The method comprises stimulating an electrode array using a set of current stimuli having different geometries, so as to provide a more regular and monotonic set of pitch percepts for a user. In one embodiment, this may be achieved by combining different modes of stimulation for a patient, so that some channels utilise one mode and other channels utilise one or more different modes.

6 Claims, 10 Drawing Sheets

IMPLANT DEVICE

This application is a continuation of Ser. No. 08/397,155 filed Apr. 3, 1995 now abandonded

TECHNICAL FIELD

The present invention relates to improvements in auditory prostheses, and more particularly to improvements in stimulation procedures and arrangements for cochlear implants.

BACKGROUND ART

The successful operation of a cochlear implant depends in part on the ability to convey pitch information. Differing pitch percepts may be produced by a cochlear implant in two distinct ways. Firstly, electrical stimulation at different sites in the cochlea excites different groups of neurons and because of the tonotopic arrangement of neurons in the cochlea, different pitch sensations result. By tonotopic is meant that the percept corresponding to a particular site in the cochlea changes in pitch from lower to higher as the site is changed in an apical to basal direction. Pitch varied in this way is known as "place pitch". Secondly different pulse rates of electrical stimulation produce different pitch sensations. Pitch varied in this way is known as "rate pitch". The current invention deals with various means of varying place pitch.

There are several commonly known methods or modes of stimulation. Each of these different known modes of operation has traditionally been employed using only one mode in each patient.

One of the current known modes used is bipolar stimulation which generally comprises passing biphasic current pulses between pairs of electrode bands, for example on a 22-band electrode array. The bands may be numbered from 1 at the basal end (broad part of the cochlea spiral, corresponding to high frequencies, near the entry point of the array) to 22 at the apical end (somewhere in the middle of the spiral, corresponding to lower frequencies). In its general sense, bipolar stimulation may involve passing current flows between any two bands. The term bipolar is also used in a specific sense to describe stimulation using two bands adjacent one another (e.g. 3 and 4) if the foregoing numbering system is utilised. More commonly, a bipolar +1 system is utilised where current flows between a band and the next but one band (e.g. 3 and 5). Similarly, "bipolar +n" systems are known where current flows between electrode k and electrode k+n+1.

Another known mode of stimulation is "monopolar" or "remote ground". In the following, when reference is made to this system, the term "monopolar" is used. In this case, current flows between one electrode inside the cochlea (possibly one of the 1 to 22 electrodes in the known system discussed above) and a single electrode somewhere outside the cochlea. This arrangement has some advantages including lower current requirements but, until now, a perceived disadvantage in precision with which current may be delivered.

Another known mode of stimulation employs a single electrode, possibly one band on the band array (22-band array discussed above) as a return electrode for all stimuli, but different first bands (e.g. 3,1; 4,1; 5,1 . . . 22 ,1). This is a particular type of bipolar (referred hereinafter as "variable bipolar") stimulation. If the return electrode is inside the cochlea it is similar to bipolar stimulation but is very similar to monopolar stimulation if the return electrode is outside the cochlea.

A still further arrangement referred to as "common ground" uses a variable first electrode and all the other electrodes are connected together as a return.

Generally, as the stimulating electrode changes (in the above-mentioned 22 band array), or in other words the site of stimulation in the cochlea, the pitch sensation changes regularly and monotonically (from high for low numbered electrodes to low for high numbered electrodes), as would be expected from the tonotopic arrangement of the cochlea. However, this is not always the case, and the pitch sensations perceived for the different modes described above are different.

The current distribution associated with stimulation of a given electrode site may also be varied by the type of electrode in the array, or more relevantly, the geometry of the electrode. There are various geometries disclosed in the prior art, including band electrodes, and sided arrays with conductive material only on part of the array surface. Use of different electrode geometries will also produce different current distributions around the site of the stimulus. In known arrangements, various electrode geometries have been used for differing purposes, however, the geometry of the intracochlear electrodes in any particular patient has been the same.

The objective of the present invention is to provide an improved arrangement for use in cochlear implant devices and an improved method of stimulating electrodes in such devices that will result in better speech perception in patients.

SUMMARY OF INVENTION

According to one aspect the present invention provides an improved method of stimulating a cochlear prosthesis, said prosthesis comprising an electrode array including a plurality of individually addressable electrodes, and a stimulator device adapted to provide electrical stimuli to selected groups of said electrodes in response to sound signals, said stimuli and the corresponding groupings of electrodes being determined by reference to a predefined instruction set, characterised in that in response to different sound signals at least two distinct current distribution geometries may be induced in the auditory structures of a user.

The variations in current distribution geometries which are referred to are intended to encompass changes in geometry, rather than mere changes in intensity. These variations may be produced by a variety of factors including selection of different modes of stimulation and use of different electrode geometries.

According to another aspect the present invention provides an auditory prosthesis, comprising an electrode array including a plurality of individually addressable electrodes, and a stimulator device adapted to provide electrical stimuli to selected groups of said electrodes in response to sound signals, said stimuli and the corresponding groupings of electrodes being determined by reference to a predefined instruction set, characterised in that in response to different sound signals at least two distinct current distribution geometries may be induced in the auditory structures of a user.

It will be appreciated that in the foregoing paragraph and in the following specification and claims a "group" of electrodes may comprise one electrode and where more than one electrode comprises a group, those electrodes may be adjacent one another or may be selected in any desired pattern from the complete array to achieve a desired beneficial result in any patient. Further the different stimulation modes may include but not be limited to any one of bipolar, variable bipolar, monopolar or common ground modes.

BRIEF DESCRIPTION OF DRAWINGS

The invention will be described with reference to the accompanying figures, in which.

DETAILED DESCRIPTION

The present invention will be more fully described in relation to the commercially available cochlear implant devices, receiver stimulator units and speech processors, particularly those available from Cochlear Pty. Ltd. However, it will be understood that the present invention may be implemented in other arrangements — the inventive concept is of broad application. Cochlear implant devices that may, although not necessarily, be employed in the performance of the present invention are the Cochlear CI1 (22 active bands on the array), the CI1 ("20+2") (20 active bands on the array and a choice of two electrodes outside the cochlear) and any similar future development. The Cochlear CI1 is the device that is presently in widespread use. The "20+2"version is essentially an experimental variant of the CI1 in which two circuit points are connected to two external electrodes instead of the two most basal bands. This allows monopolar stimulation.

Figure 8:
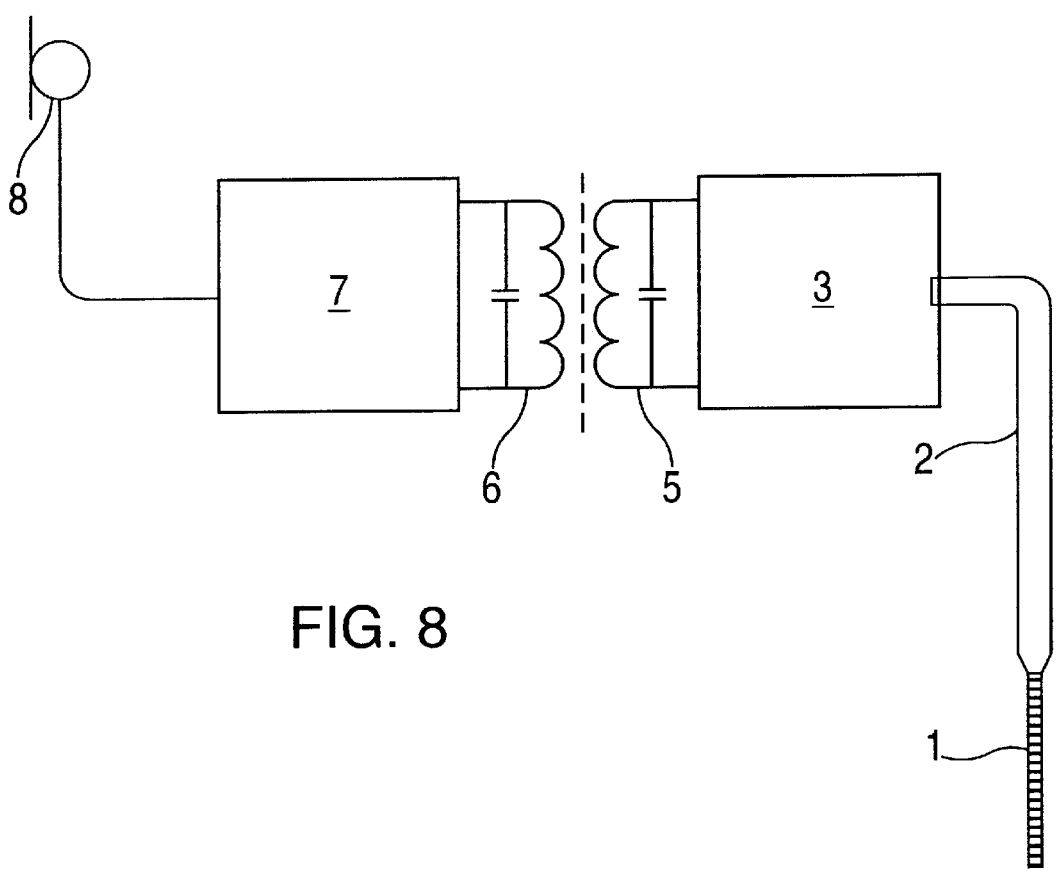
FIG. 8 illustrates the general arrangement of a cochlear implant system.
Figure 9A:
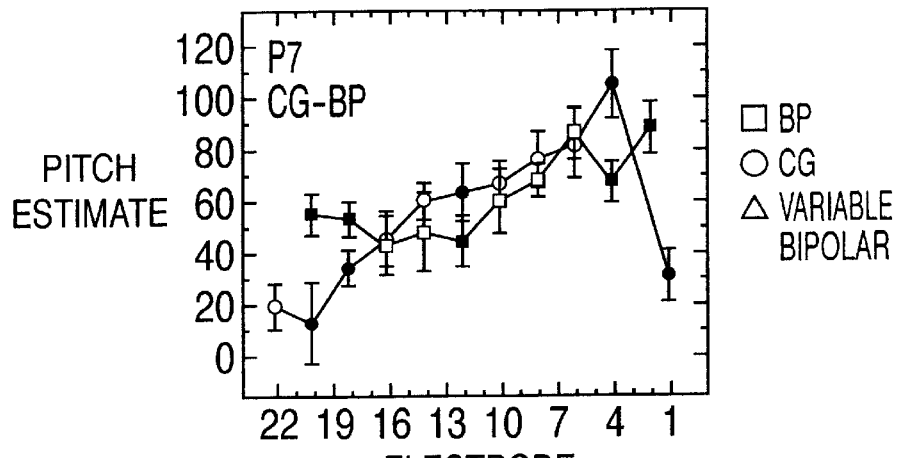
FIG. 9 illustrates a further set of pitch estimates for different modes in three patients P7, P8, P9.
Figure 9B:
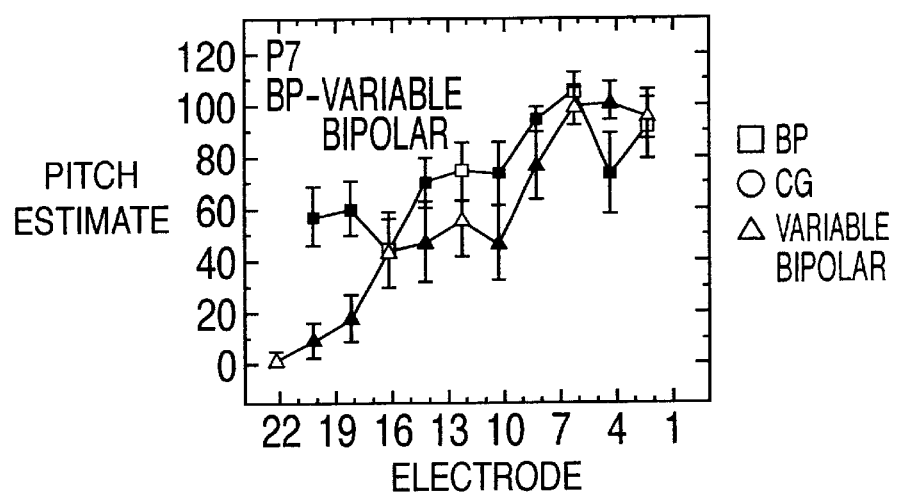
Figure 9C:
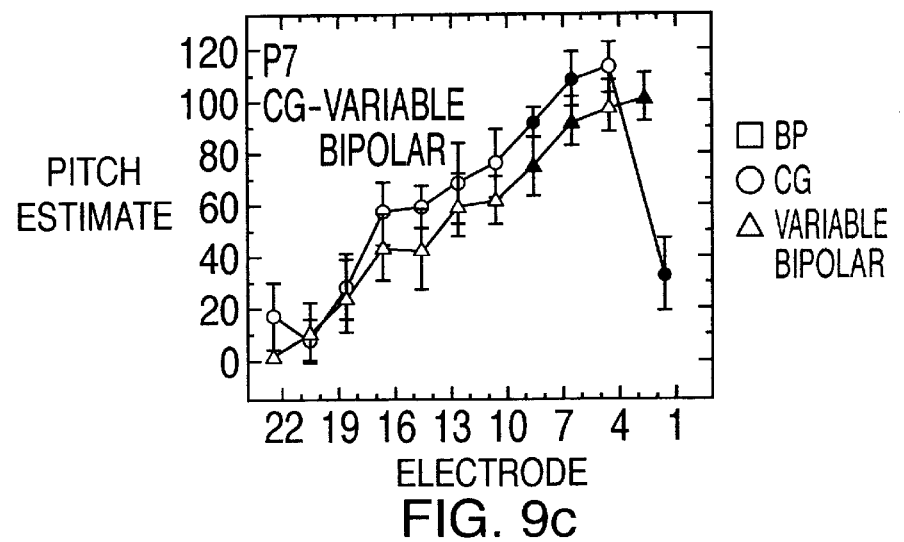
Figure 9D:
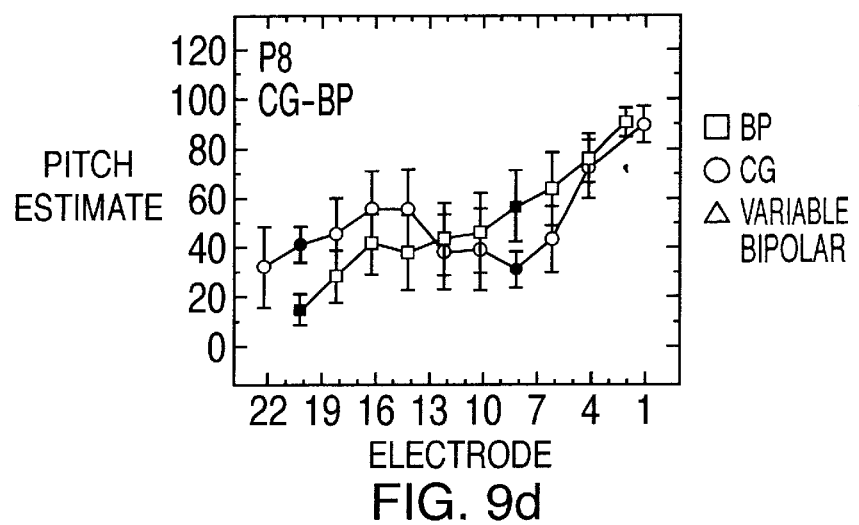
Figure 9E:
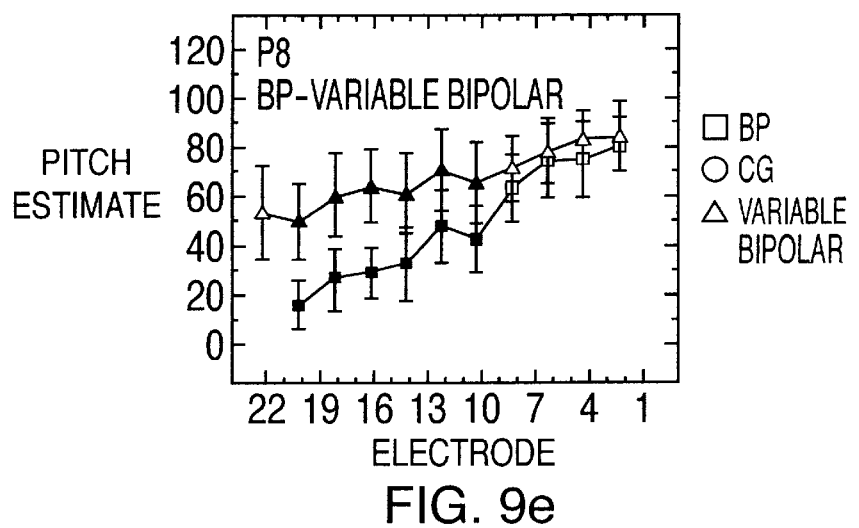
Figure 9F:
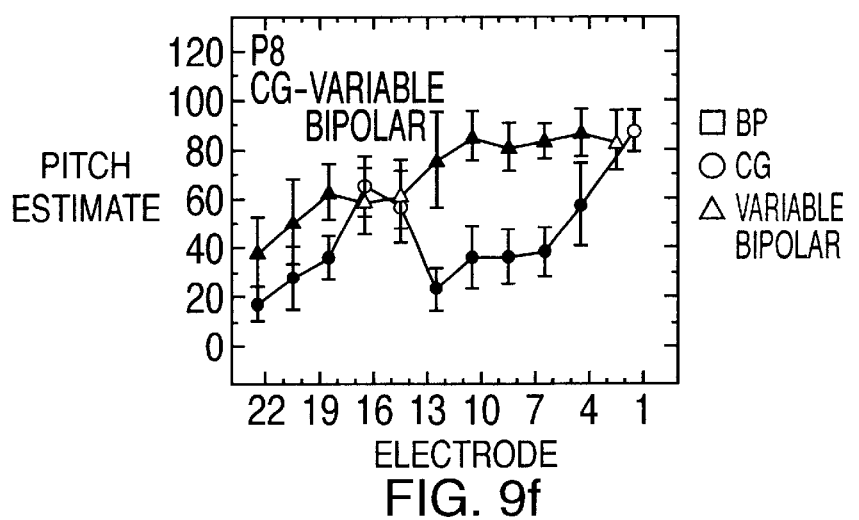
Figure 9G:
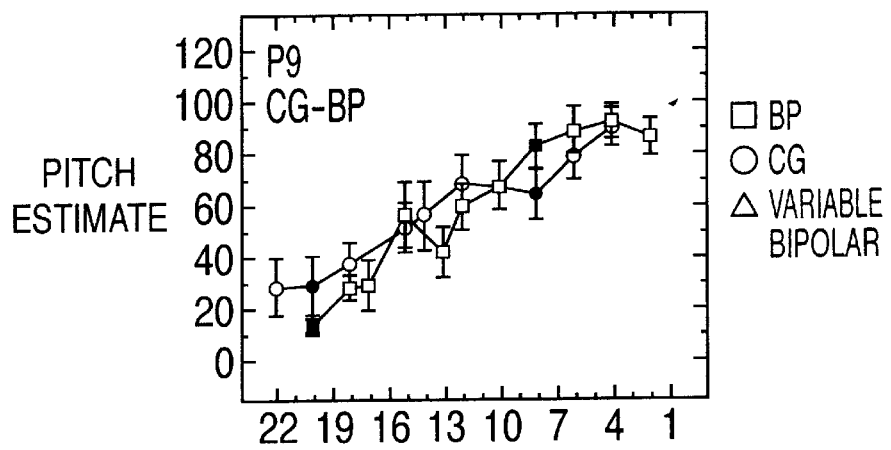
Figure 9H:
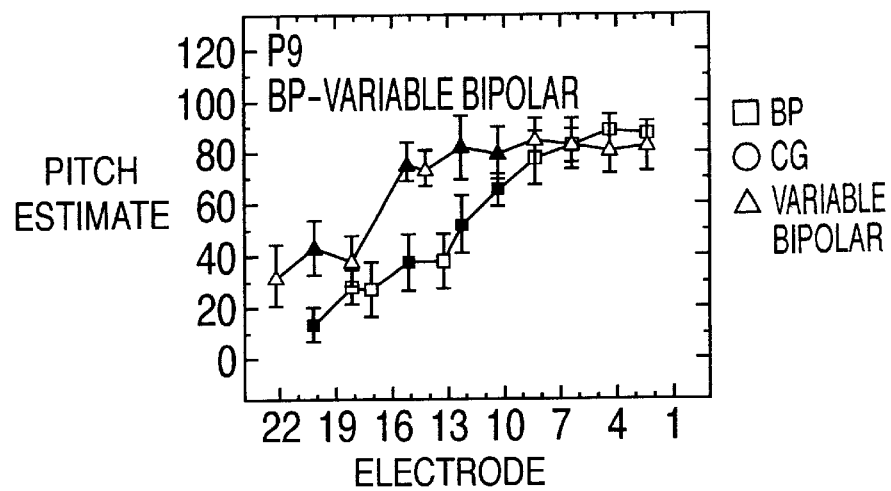
Figure 9I:
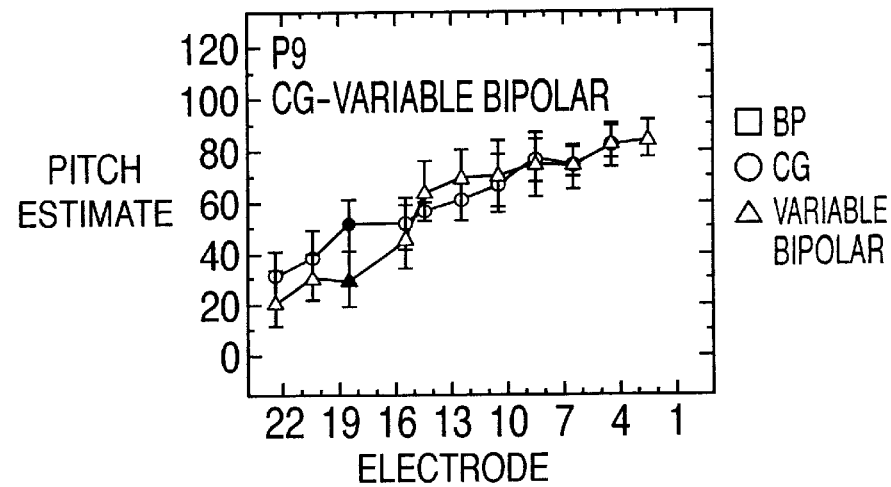

The general arrangement may be understood with reference to FIG. 8. The reader will be aware of the principles generally used in construction and operation of such an arrangement, and so only a general overview will be provided.

Sound signals are detected by microphone 8, and passed to speech processor 7. Processor 7 analyses the incoming sound signal and produces a set of stimulus instructions for the electrode array 1. Various techniques for speech processing are known to those skilled in this field, and the present invention is not dependant on any particular form of processing being employed. Power and signals are communicated to the receiver/stimulators unit (RSU)3, preferably via a transcutaneous inductive link 5, 6. The RSU 3 provides stimuli to selected electrodes of electrode array 1 via the wire connection 2. The stimuli are preferably short biphasic pulses.

It will be appreciated that conventional devices allow for the selection of the mode of stimulation and may be used to provide the combined mode stimulation according to an embodiment of the present invention.

The present invention provides an improved stimulation arrangement by recognising that utilising different geometries of current distribution for a single implanted array can enable a better range of pitch percepts for the patient. Instead of a stimulation pattern which is, for example, fixed in bipolar +1 mode for all electrodes, a mixture of modes may be used for different electrodes, for example. Similarly, the electrode geometry may be varied within the array, to allow for different sites within the cochlea to be stimulated by different geometries of current distribution, and so produce an improved set of pitch percepts. These changes operate to change the current distribution associated with stimulation at a given implanted site, which alters the associated pitch percept and allows for a wider range of possible pitch percepts to be delivered.

For example, some patients might obtain an optimum result if bipolar+1 stimulation was used on the basal electrodes and monopolar stimulation was used on the more apical electrodes. The present Cochlear array (in its standard bipolar mode) provides "longitudinal" stimulation, as current flows between two bands at different positions along the array. "Radial" stimulation is another possibility. In such a case, a band might be split, and current might flow between the halves of the band. It will be appreciated that the use of a specialised array, in which for example certain electrodes are split rings and the remainder are bands, is a means of implementing the present invention.

Studies carried out by the inventors provide support for the need to develop an invention of the type described here, by the use of which the place pitch perceived by a patient may be improved. These studies have been made regarding pitch estimation for different modes of stimulation with either standard electrode insertion depths or with deep electrode insertions. In a first of these studies nine postlinguistically deafened adult patients with electrode arrays inserted to standard depths were investigated. Pitch estimates for stimulating electrodes along the electrode array were then determined using bipolar, common ground and "variable bipolar" stimulation (i.e. in this case between individual electrodes along the array and the most basal electrode on the array). At the maximum comfort level of the patients, pitch was measured using a single interval numerical estimation method similar to that used in previous studies on pitch estimation for electrical stimulation (Shannon, 1983; Dorman et al., 1990), and this is the basis for the left hand scale on the pitch estimates graphs in the accompanying figures.

The results of this investigation as shown in part in the accompanying FIG. 9 indicated some differences to the expected regularity and monotonicity of pitch estimations. It was also observed when using "variable bipolar" stimulation that a reduced range for pitch for patients occurred when the return electrode was internal to the cochlea. Individual differences in pitch estimations were also observed among the three modes of stimulation for most patients. Furthermore, current levels needed to achieve threshold (T) and comfortable listening (C) levels varied with the mode of stimulation employed. No consistent pattern emerged with threshold and comfortable listening levels for bipolar stimulation. With variable bipolar stimulation threshold and comfortable listening levels increased in an apical to basal direction for most patients. Perhaps this was to be expected because of the narrowing spatial extent. With common ground stimulation, there was a tendency for threshold and comfortable listening levels to be higher for electrodes in the middle of the array rather than either end of the array. The size of the dynamic range when common ground stimulation was used seemed to be substantially equivalent to that using bipolar stimulation and was usually greater than for variable bipolar stimulation.

FIG. 1 illustrates the results of another study of pitch estimations for 6 subjects with deeply inserted electrode arrays. In addition to the bipolar +1 stimulation used on all subjects, monopolar was also used for subjects S5 and S6. This shows departures from the expected regular variation of pitch estimate with electrode for four patients (S3, S4, S5, S6) for bipolar+1 stimulation, and for two subjects with monopolar stimulation (S5, S6). For each patient, N is the number of repetitions, and the accompanying key indicates the differing percepts obtained for some patients using bipolar+1, monopolar with ball electrode (MONO-B), and monopolar with plate electrode (MONO-P). Pulsedur is the pulse duration in for each phase of the biphasic pulse each case in $\mu$s.

These investigations support the need for this invention in which the place pitch perceived by a patient may be improved by utilizing more than one mode of stimulation in the one patient.

FIGS. 2 to 7 illustrate examples of the use of combining modes to produce a more appropriate pitch set for a given patient. It is emphasised that in any given case detailed study needs to be made of responses by the patient to design an optimum pitch set for that patient. In some patients, the present invention may not be required, or may be ineffective — this needs to be determined on a case by case basis, and desirable pitch sets will not always be achievable. In general, it is greatly desirable to produce a pitch set in which stimulation of progressively more apical electrodes results in a regularly and monotonically decreasing pitch percept.

Figure 1A:
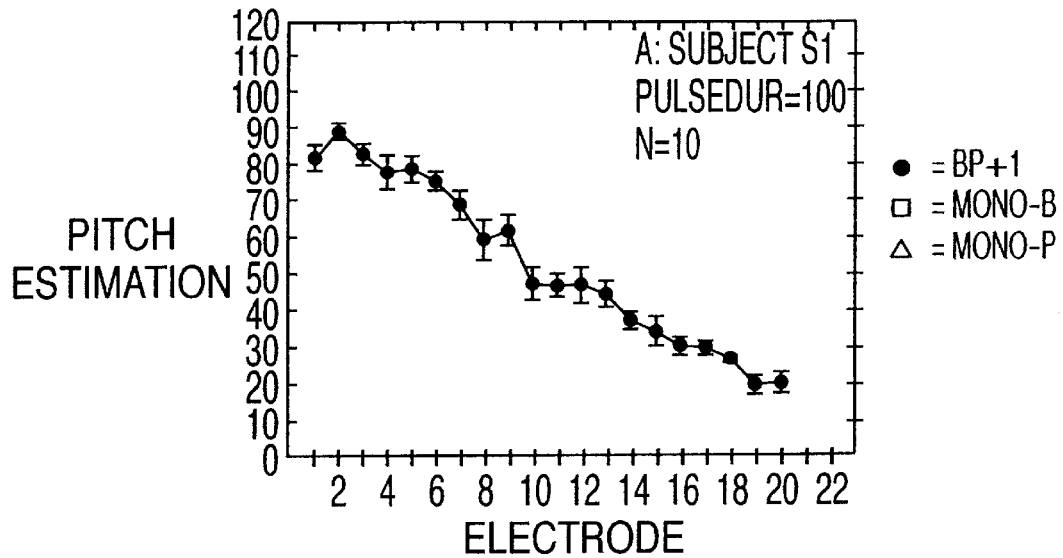
FIG. 1 illustrates estimates of pitch for several patients.
Figure 1B:
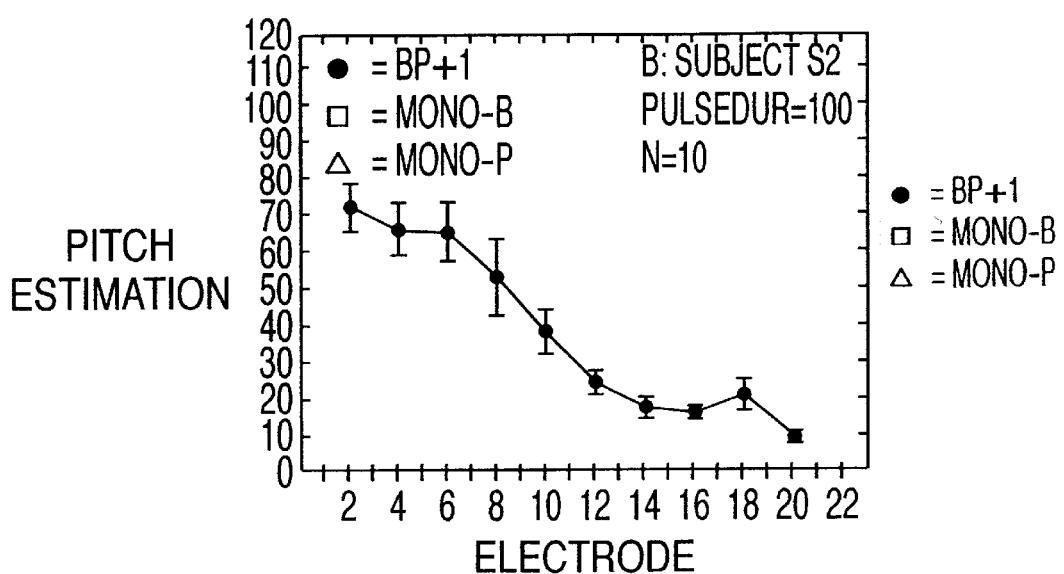
Figure 1C:
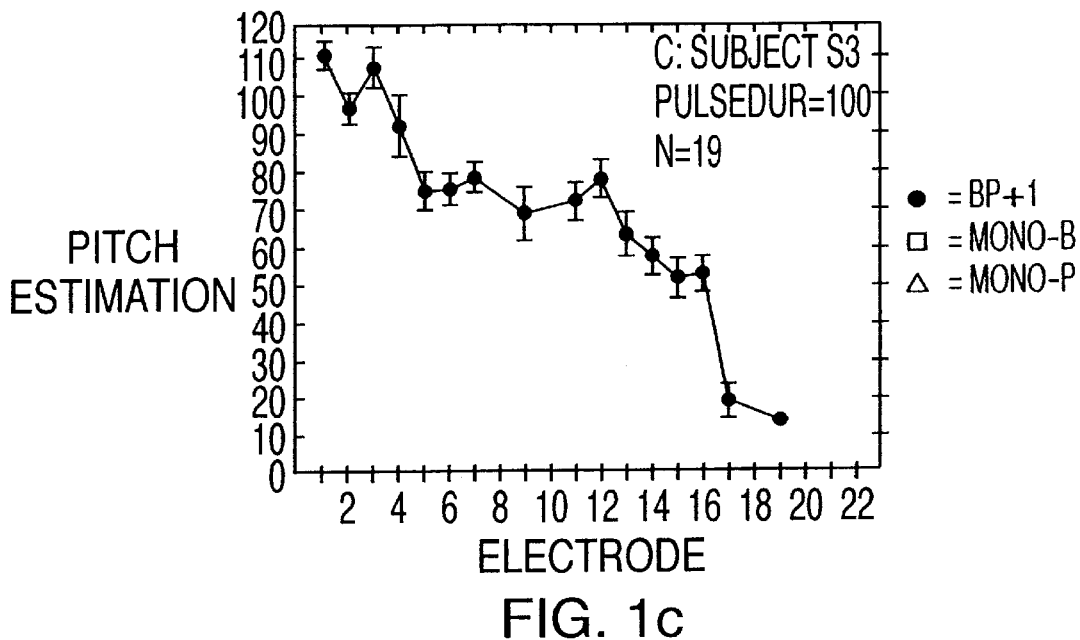
Figure 1D:
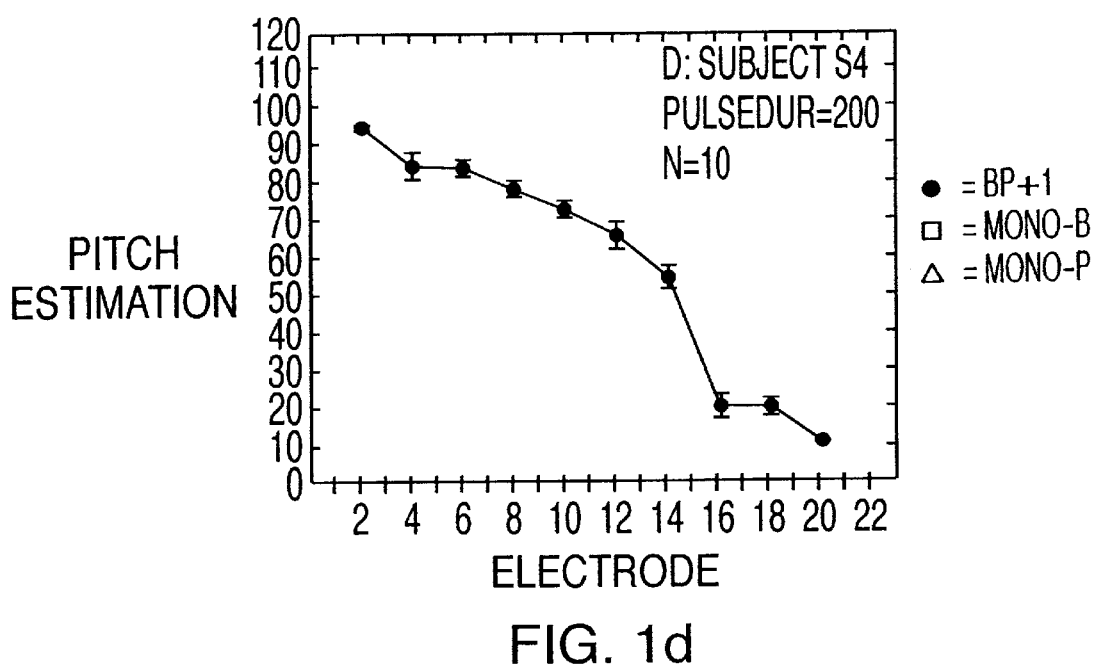
Figure 1E:
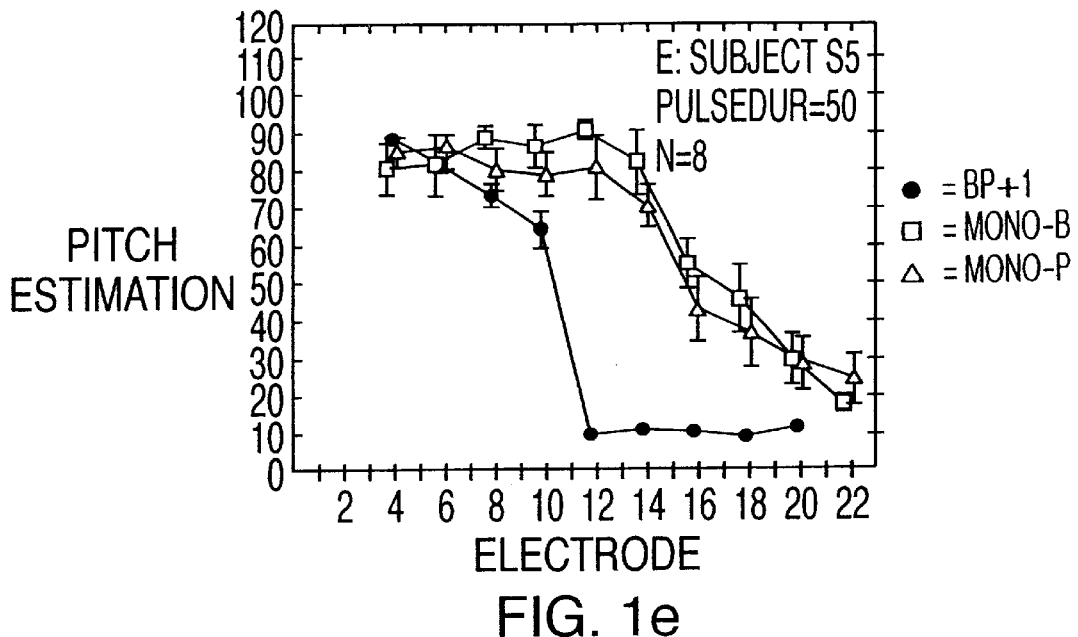
Figure 1F:
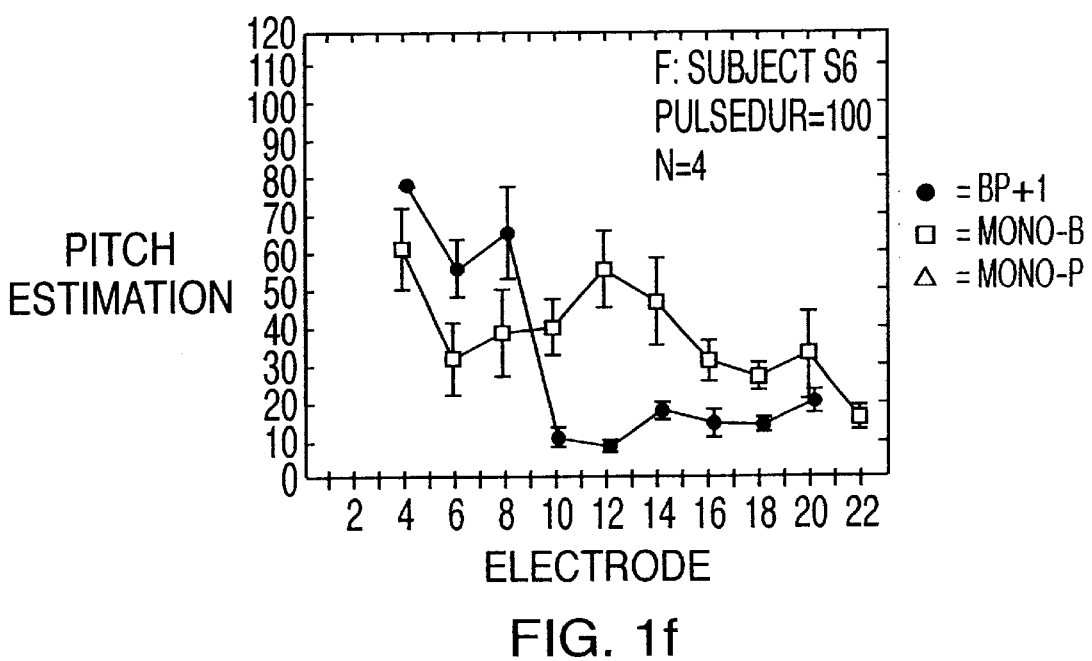
Figure 2:
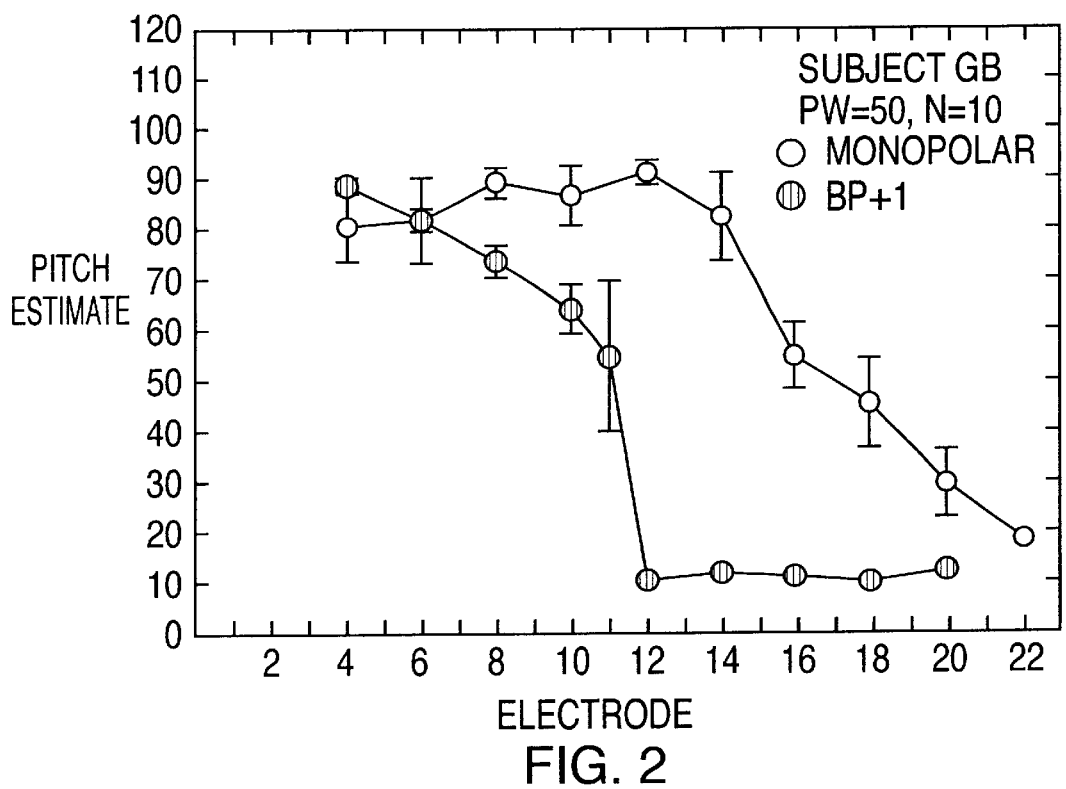
FIGS. 2, 4 and 6 illustrates pitch estimations by patients in response to stimulation in different modes.
Figure 3:
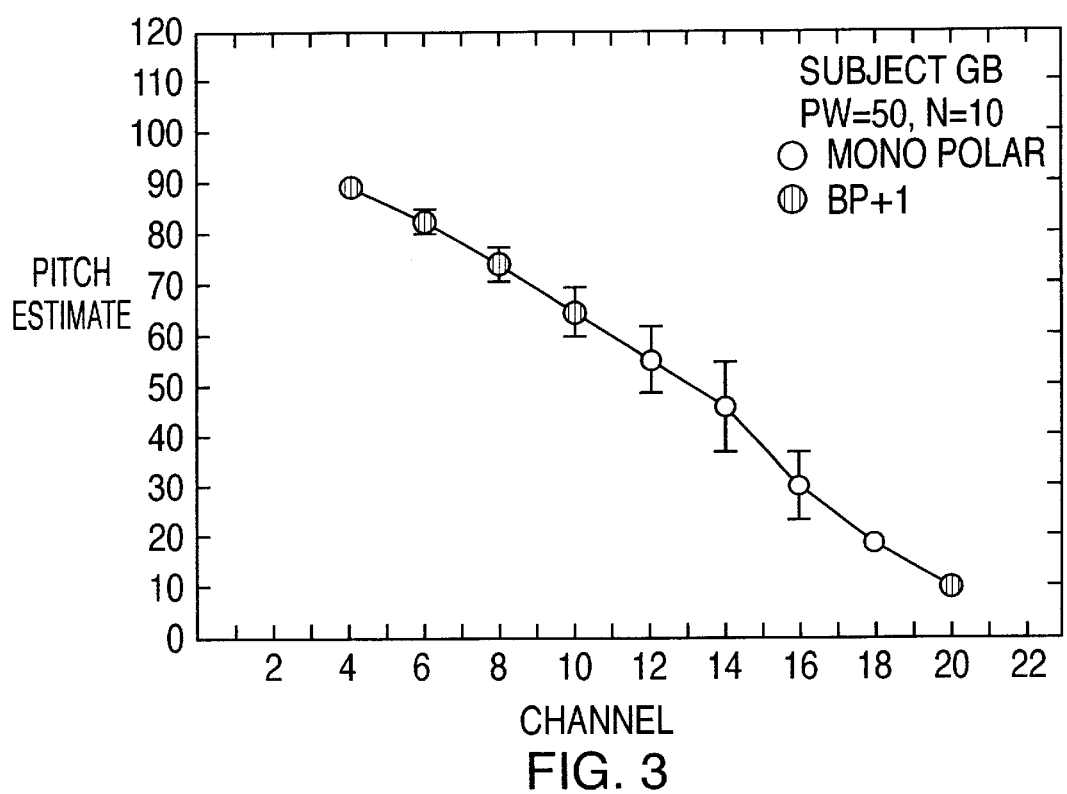
FIGS. 3, 5 and 7 illustrate pitch maps using combined modes.

Referring to FIG. 2, (taken from FIG. 1) a comparison of the percepts for monopolar and bipolar +1 modes shows a relatively flat response with monopolar mode for the more basal electrodes, and a more desired outcome above electrode 12. Conversely, the pitch percepts for bipolar+1 mode above electrode 12 show little variation, however, regular and monotonic percepts were recorded at the basal end. FIG. 3 shows a pitch set for the same patient as in FIG. 2, where the modes of stimulation have been mixed to provide a more regular outcome.

Figure 4:
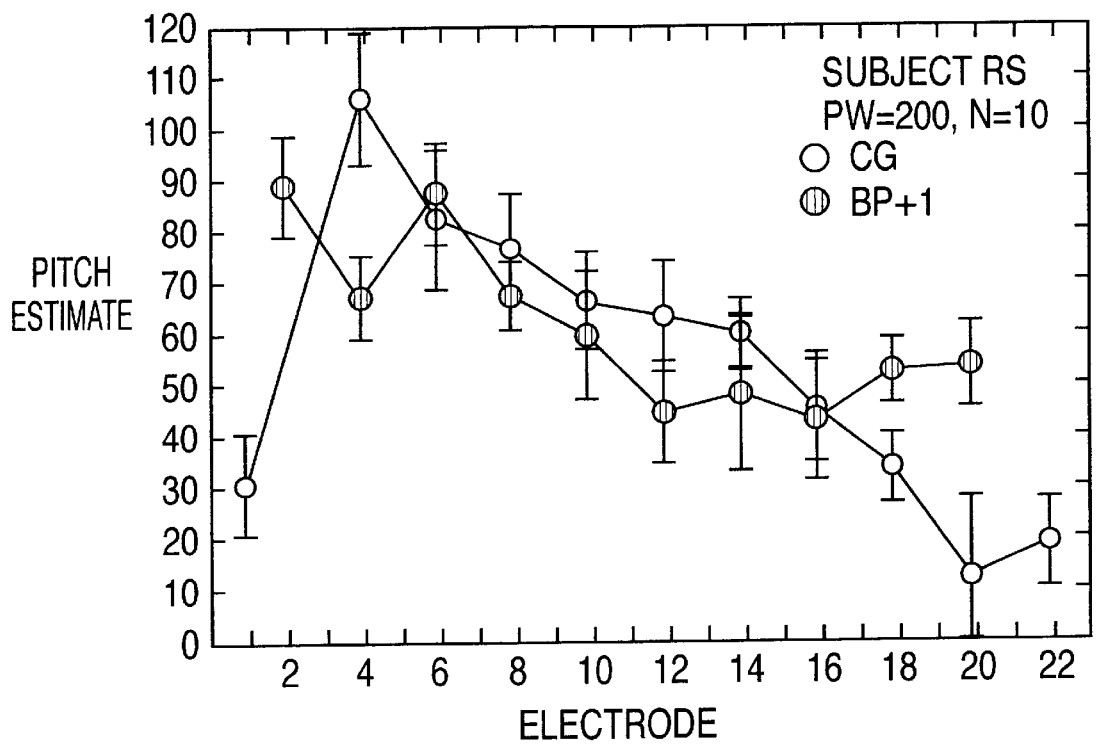
Figure 5:
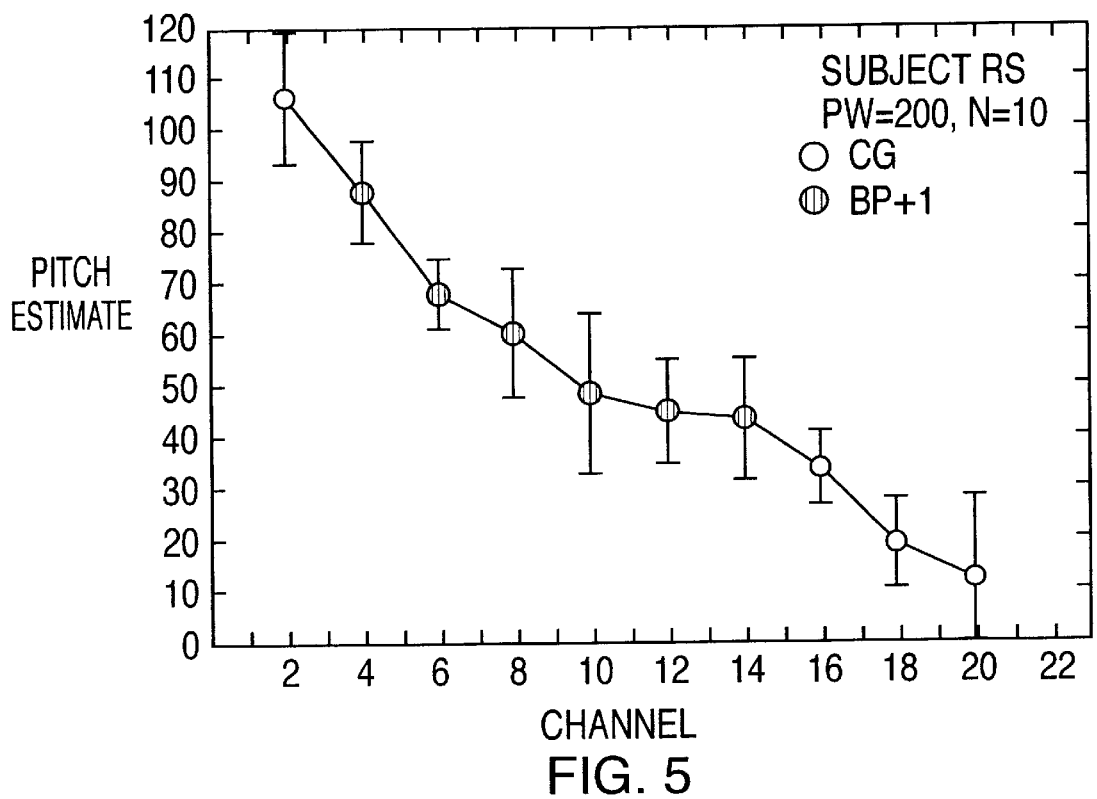

FIG. 4 (taken from FIG. 9) illustrates for another patient the percepts obtained for common ground, and those obtained for bipolar+1 mode. FIG. 5 shows a pitch set derived by combining the common ground and bipolar+1 modes for this patient. Again, a much more regular pitch set can be derived than from either alone.

Figure 6:
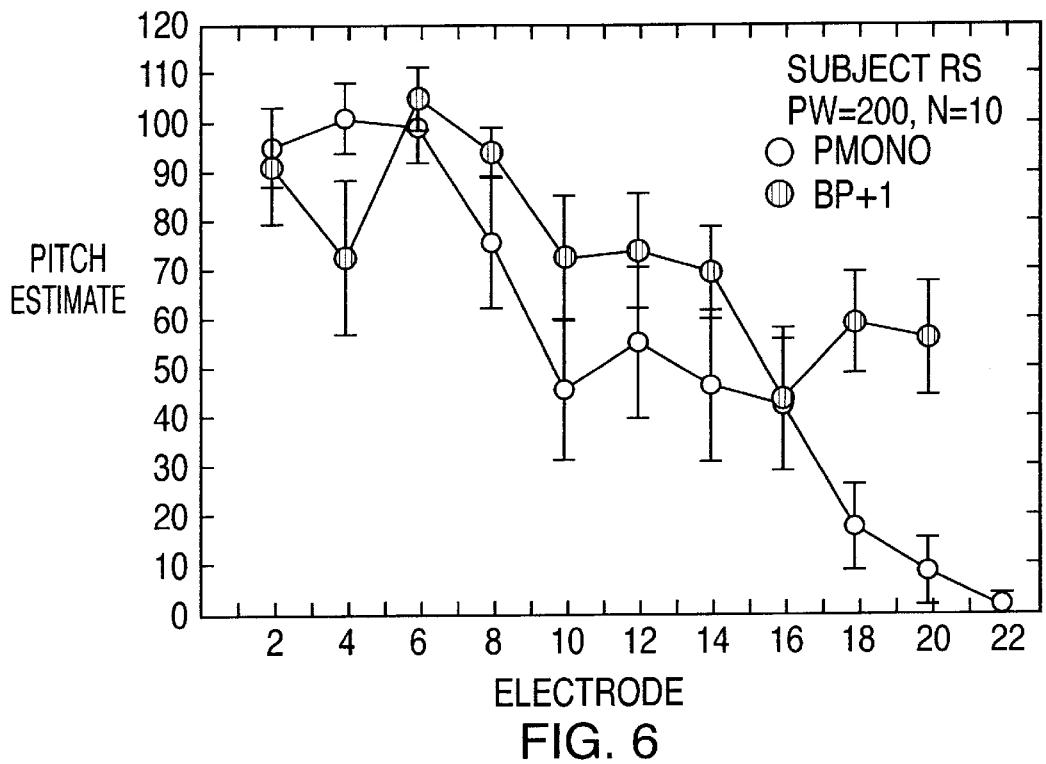
Figure 7:
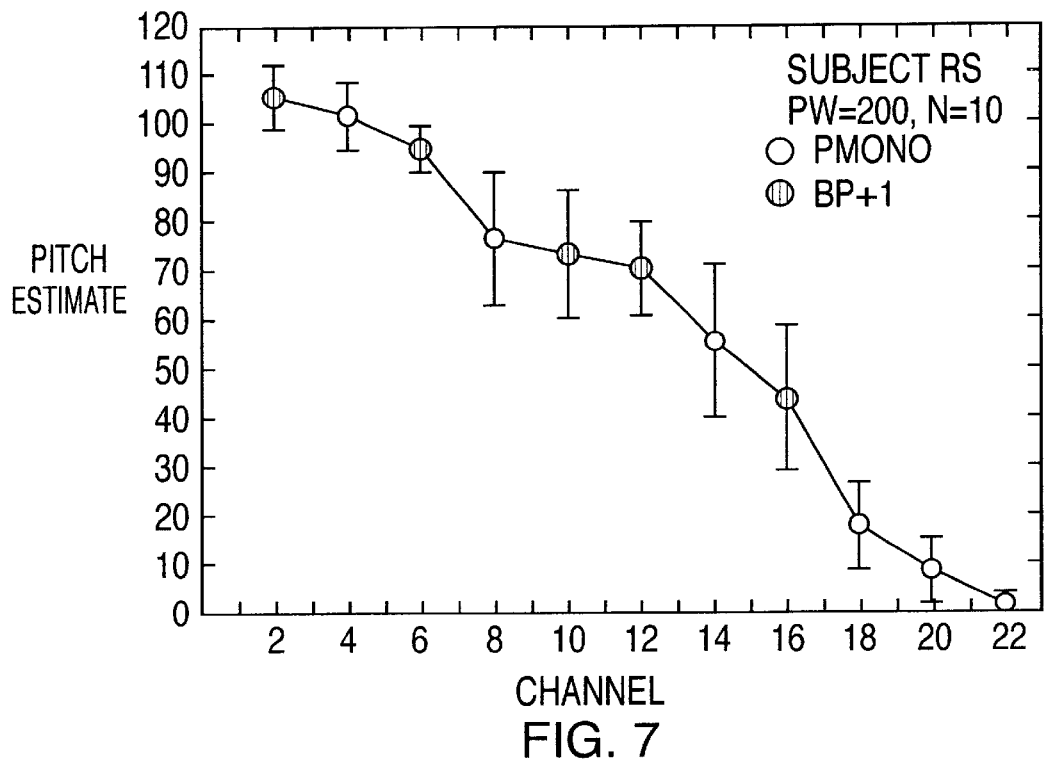

FIG. 6 (taken from FIG. 9) illustrates variable bipolar mode and bipolar+1 mode percepts for another patient. By variable bipolar is meant in this case utilising electrode 1 as the return electrode. As this patient has several bands outside the cochlea, this is very similar to monopolar for this patient. FIG. 7 provides a pitch set combining the variable bipolar and bipolar+1 modes. Again, a much more regular pattern of pitch percepts can be obtained.

It will be appreciated that other techniques for varying the current distribution associated with a given stimulation site may be used to provide further differences in pitch percepts, so as to select a pitch set for a given patient so as to produce a more regular and monotonic function. Further, the use of techniques such as composite pitch to provide pitch percepts not perceived with any given electrode site under, say, bipolar+1 stimulation can provide additional percepts to those possible using a single mode alone. It will be appreciated that while the discussion above has predominantly been concerned with combining modes, variation of other aspects as discussed, and combinations of, say, electrode geometry variations and mode variations are contemplated within the scope of the present invention.

What is claimed is:

1. A method of generating an instruction set for a cochlear prosthesis used to treat a particular patient, said cochlear prosthesis including a plurality of individually addressable electrodes and a stimulation device adapted to provide electrical stimuli to selected groups of electrodes in accordance with said instruction set, each group of electrodes defining a specific current distribution geometry, said method comprising:

generating a plurality of test signals defining a frequency band;

stimulating the patient's aural nerve by applying said test signals to each of said group using a plurality of modes of stimulation, each mode generating a different one of said current distribution geometries;

measuring responses of the patient to the test signals;

matching each test signal to one of said modes of stimulation on the basis of the said measured responses so as to produce an optimal response to the respective test signal; and setting said instruction set to select for each signal of a particular frequency the corresponding group based on said matching.

2. The method of claim 1 further comprising applying stimuli to said groups in accordance with modes of stimulation, each mode corresponding to a matching pair.

3. The method of claim 2 wherein said modes of stimulation are selected from the stimulation group consisting of monopolar, bipolar, variable polar and common ground modes of stimulation.

4. The method of claim 1 wherein electrodes include a first set of electrodes having a first geometry and a second set of electrodes having a second geometry, comprising the step of selecting a first group to include said first set of electrodes and selecting a second group to include said second set of electrodes.

5. The method of claim 1 comprising determining said optimal responses by stimulating progressively more apical electrodes to obtain a monotonically decreasing pitch precept.

6. The method of claim 1 wherein different modes of stimulation is applied respectively to each group, said modes being selected to define a substantially linear response as a function of said sounds.

* * * * *